United States Patent

Nakane

Patent Number: 4,639,461
Date of Patent: Jan. 27, 1987

[54] 7-OXABICYCLOHEPTANE SUBSTITUTED KETO-AMIDE PROSTAGLANDIN ANALOGS USEFUL IN THE TREATMENT OF THROMBOTIC DISEASE

[75] Inventor: Masami Nakane, Hopewell, N.J.

[73] Assignee: E. R. Squibb & Sons, Inc., Princeton, N.J.

[21] Appl. No.: 791,819

[22] Filed: Oct. 28, 1985

[51] Int. Cl.$^4$ .................. A61K 31/557; C07D 307/00; C07D 405/08
[52] U.S. Cl. .................................. 514/382; 514/469; 548/253; 549/463
[58] Field of Search .................. 549/463; 548/253; 514/469, 382

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |
| 4,416,896 | 11/1983 | Nakane et al. | 549/463 |
| 4,456,617 | 6/1984 | Nakane et al. | 549/463 |

FOREIGN PATENT DOCUMENTS 0043292 8/1982 European Pat. Off.
2039909 8/1980 United Kingdom.

Primary Examiner—Henry R. Jiles
Assistant Examiner—Bernard H. Dentz
Attorney, Agent, or Firm—Lawrence S. Levinson; Burton Rodney

[57] ABSTRACT

7-Oxabicycloheptane substituted keto-amide prostaglandin analogs are provided having the structural formula

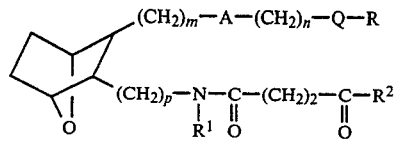

wherein m is 0 to 4; A is $-CH=CH-$ or $-CH_2-CH_2-$; n is 1 to 5; Q is $-CH=CH-$, $-CH_2-$,

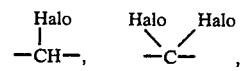

or a single bond; R is $CO_2H$, $CO_2$alkyl, $CO_2$alkali metal, $CO_2$polyhydroxyamine salt,

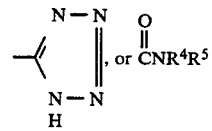

wherein $R^4$ and $R^5$ are the same or different and are H, lower alkyl, hydroxy, lower alkoxy or aryl, at least one of $R^4$ and $R^5$ being other than hydroxy and lower alkoxy; p is 1 to 4; $R^1$ is H or lower alkyl; and $R^2$ is H, lower alkyl, lower alkenyl, aryl, arylalkyl, cycloalkyl or cycloalkylalkyl.

The compounds are cardiovascular agents useful, for example, in the treatment of thrombotic disease.

15 Claims, No Drawings

7-OXABICYCLOHEPTANE SUBSTITUTED KETO-AMIDE PROSTAGLANDIN ANALOGS USEFUL IN THE TREATMENT OF THROMBOTIC DISEASE

DESCRIPTION OF THE INVENTION

The present invention relates to 7-oxabicycloheptane substituted keto-amide prostaglandin analogs which are cardiovascular agents useful, for example, in the treatment of thrombotic disease. These compounds have the structural formula

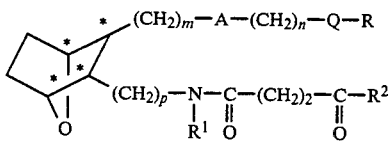

including all stereoisomers thereof, wherein m is 0 to 4; A is —CH=CH— or —CH$_2$—CH$_2$—; n is 1 to 5; Q is —CH=CH—, —CH$_2$—,

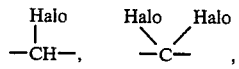

or a single bond; R is CO$_2$H, CO$_2$alkyl, CO$_2$ alkali metal, CO$_2$polyhydroxyamine salt,

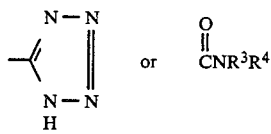

wherein R$^3$ and R$^4$ are the same or differnt and are H, lower alkyl or aryl; p is 1 to 4; R$^1$ is H or lower alkyl; and R$^2$ is H, lower alkyl, lower alkenyl, aryl, arylalkyl, cycloalkyl or cycloalkylalkyl.

The term "lower alkyl" or "alkyl" as employed herein alone or as part of another group includes both straight and branched chain hydrocarbon radicals of up to 12 carbons such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkylaryl substituent, a haloaryl substituent, a cycloalkyl substituent, an alkylcycloalkyl substituent, hydroxy, an amino substituent, an amido substituent, an alkylamino substituent, an arylamino substituent, an alkanoylamino substituent, an arylcarbonylamino substituent, a thioamido substituent, a nitro substituent, a cyano substituent, a thiol substituent, an arylthio substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups 1 or 2 lower alkoxy groups. 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 amino groups, 1 or 2 alkylamino groups, 1 or 2 arylamino groups, 1 or 2 alkanoylamino groups, 1 or 2 arylcarbonylamino groups, 1 or 2 amido groups, 1 or 2 nitro groups, 1 or 2 cyano groups, 1 or 2 thioamido groups, 1 or 2 thiol groups, 1 or 2 arylthio groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy" or "aralkoxy" as employed herein alone or as part of another group includes any of the above lower alkyl, alkyl or aralkyl groups linked to an oxygen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like and may be substituted by any of the substituents set out hereinbefore with respect to the definition of the "alkyl" group.

The terms (CH$_2$)$_m$, (CH$_2$)$_n$, and (CH$_2$)$_p$ includes straight or branched chain radicals having from 0 to 4 carbons in the normal chain in the case of (CH$_2$)$_m$, from 1 to 5 carbons in the normal chain in the case of (CH$_2$)$_n$ and from 1 to 4 carbons in the normal chain in the case of (CH$_2$)$_p$ and may contain one or more lower alkyl and/or halogen substituents. Examples of (CH$_2$)$_m$, (CH$_2$)$_n$, and (CH$_2$)$_p$ groups include

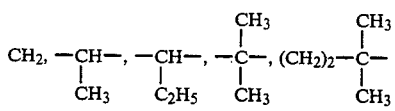

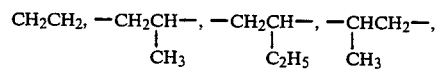

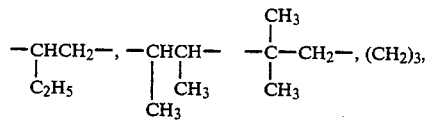

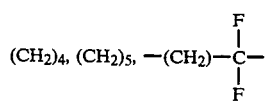

-continued

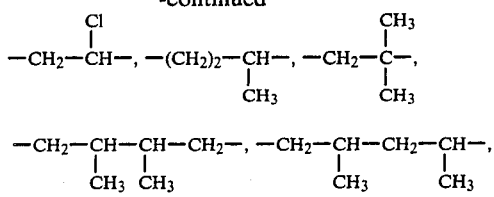

and the like.

The term "amide" refers to the group

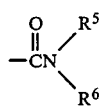

wherein $R^5$ and $R^6$ are independently hydrogen, lower alkyl or aryl.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those compounds of formula I wherein m is 1, A is a —CH=CH—, n is 3 or 4, Q is a single bond or —C($F_2$)—, ($CH_2$)$_2$, or —CH=CH, R is $CO_2H$; p is 1, $R^1$ is H; and $R^2$ is arylalkyl such as benzyl or phenylethyl, or lower alkyl, such as pentyl, hexyl, or heptyl.

The compounds of formula I of the invention may be prepared as described below.

A. p is 1, m is 1, Q is —$CH_2$— or a single bond and $R^1$ is H

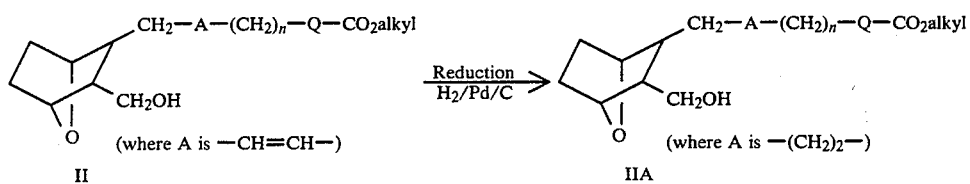

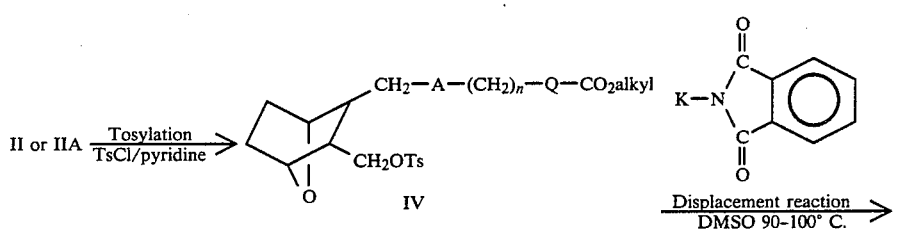

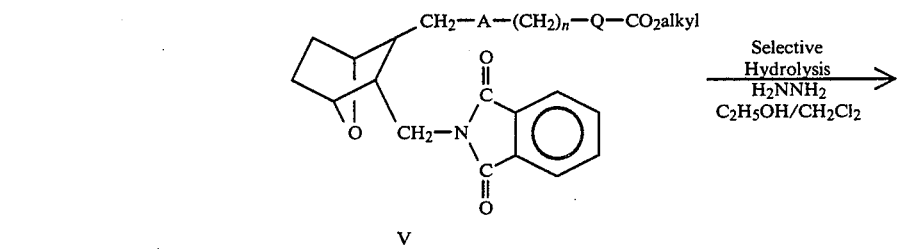

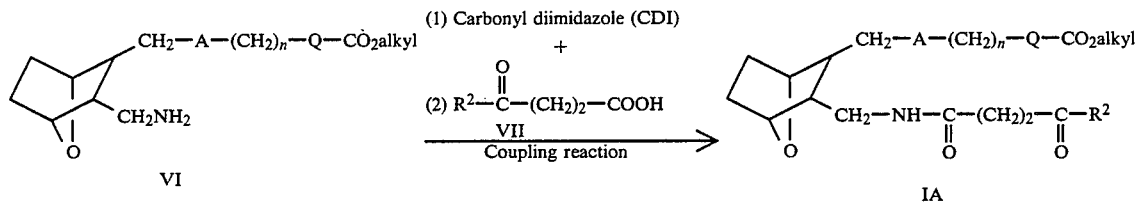

A'. Where p is 1, m is 1, Q is —$CH_2$— or a single bond and $R^1$ is alkyl.

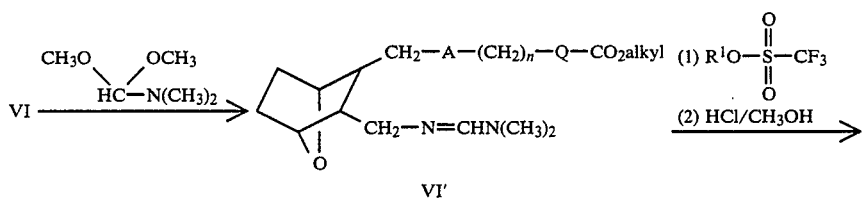

-continued
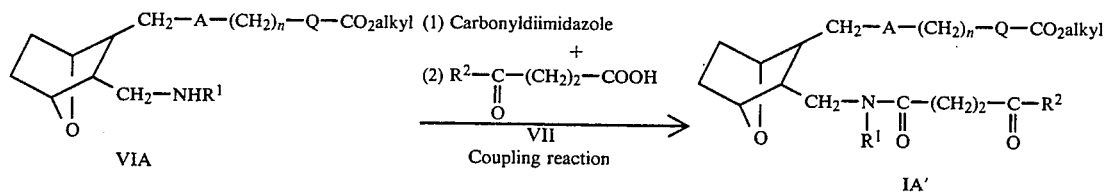
B. Where Q is CH$_2$ or a single bond, p is 2 to 5, m is 1 and R$^1$ is H
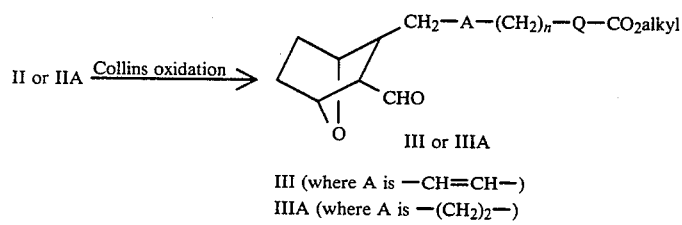
III (where A is —CH=CH—)
IIIA (where A is —(CH$_2$)$_2$—)
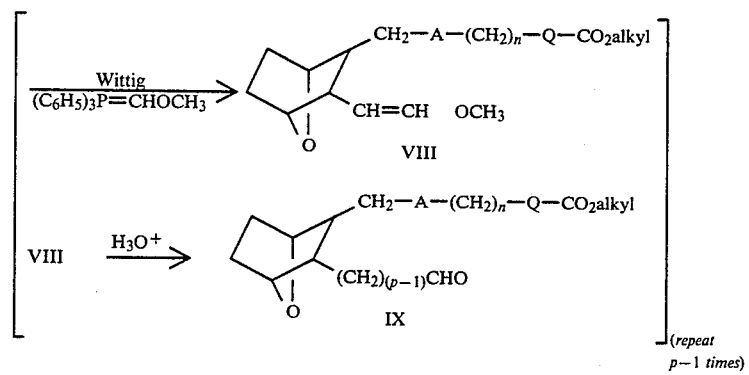
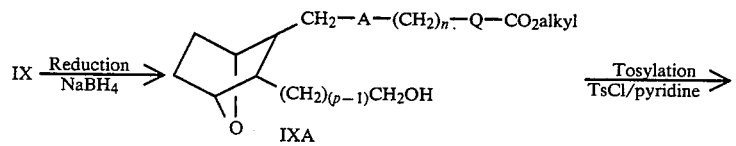
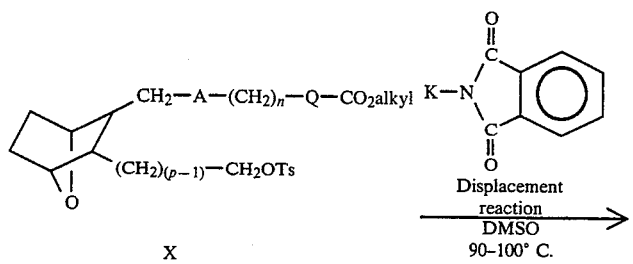
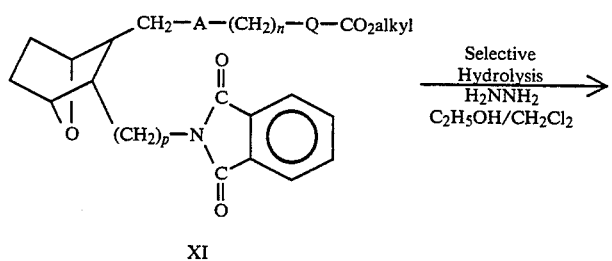

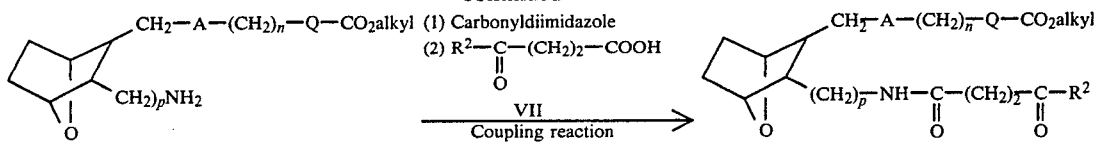
XII → IB
B'. Where Q is CH₂ or a single bond, p is 2 to 5, m is 1 and R¹ is alkyl
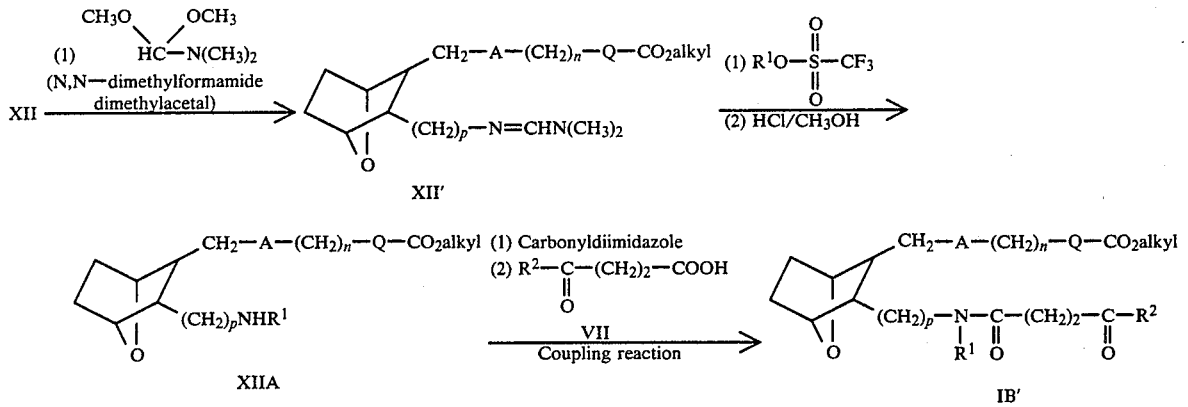
C. Where m is 2, p is 1, A is —CH=CH— and Q is CH₂ or a single bond
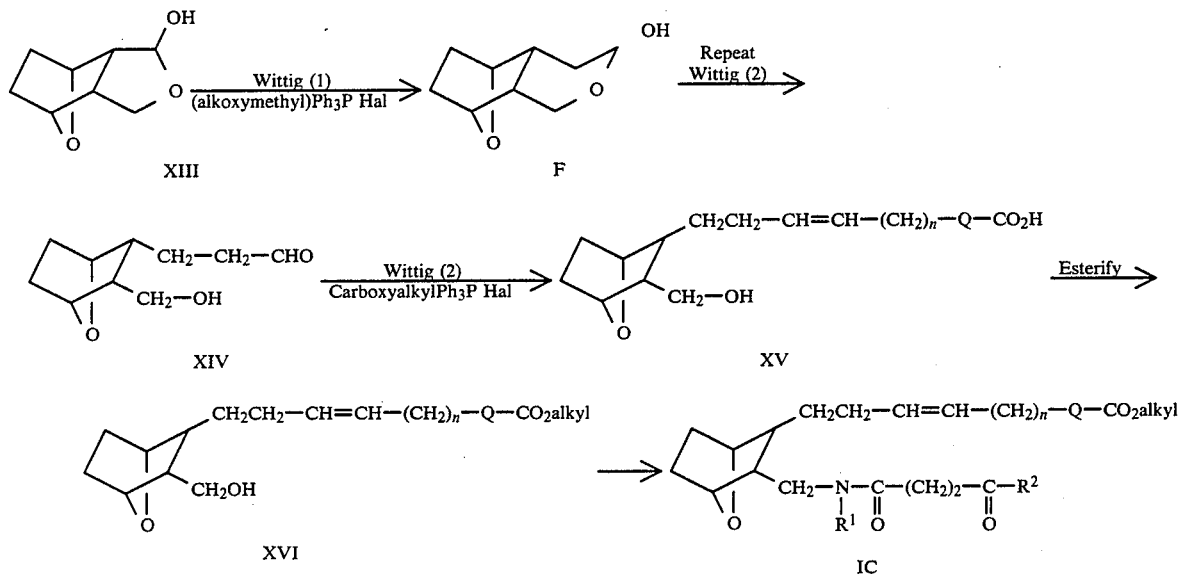
D. m is 2, p is 1, A is —CH₂—CH₂— and Q is CH₂ or a single bond
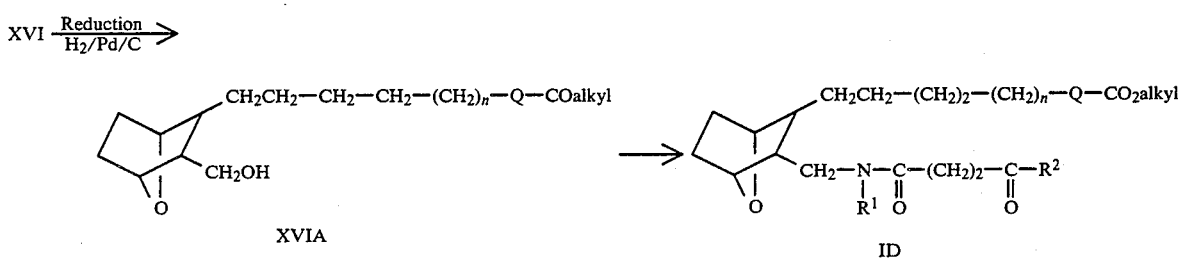
E. Where m is 3 or 4, p is 1, A is —CH=CH— and Q is CH₂ or a single bond
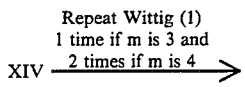

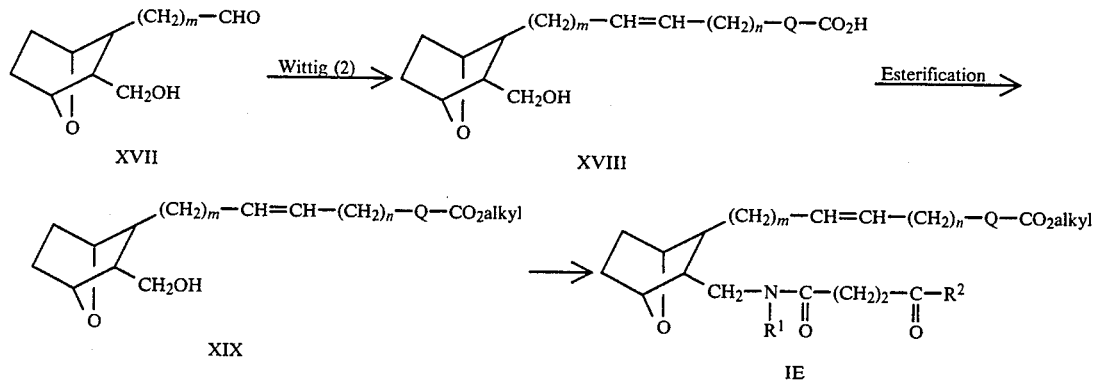
F. Where m is 3 or 4, p is 1, A is $CH_2CH_2$ and Q is $CH_2$ or a single bond
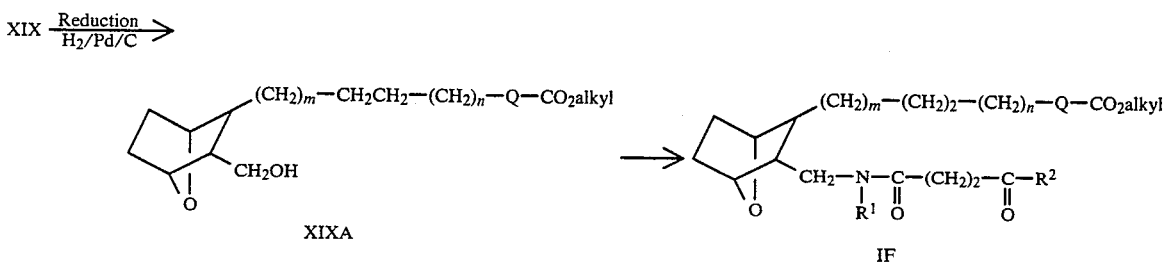
G. Where m = 0, A is —CH=CH—, p is 1, Q is $CH_2$ or a single bond
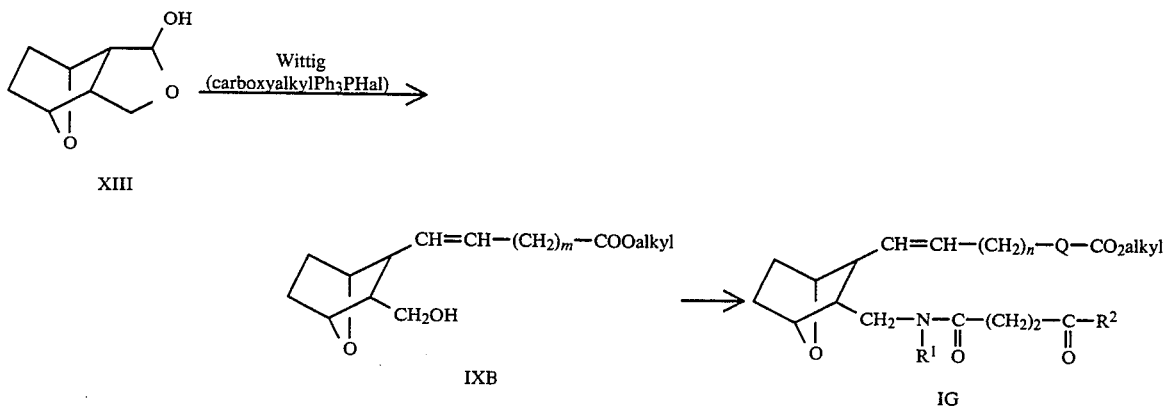
H. Where m = 0, A is —$(CH_2)_2$—, p is 1, Q is $CH_2$ or a single bond
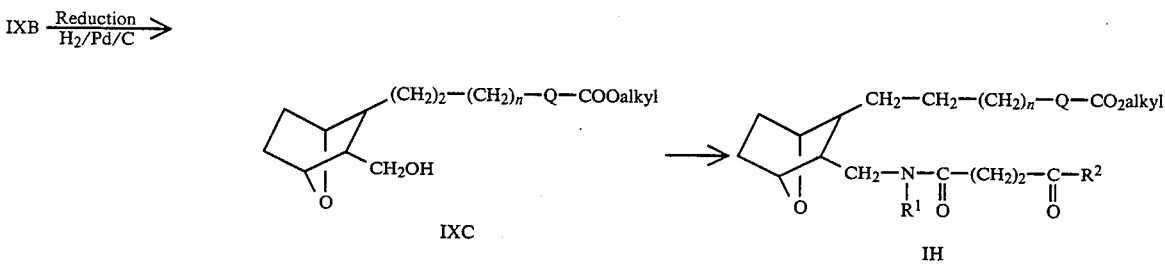
I. Where Q is —CH=CH—
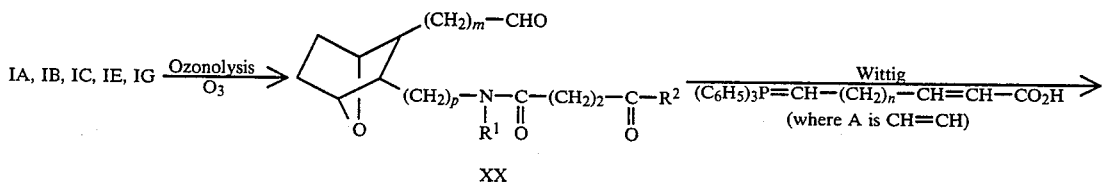

4,639,461

-continued

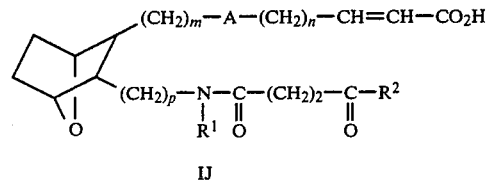

IJ

J. Where Q is $-\overset{\text{halo}}{\underset{|}{\text{CH}}}-$ or $-\overset{\text{halo}}{\underset{\text{halo}}{\overset{|}{\text{C}}}}-$

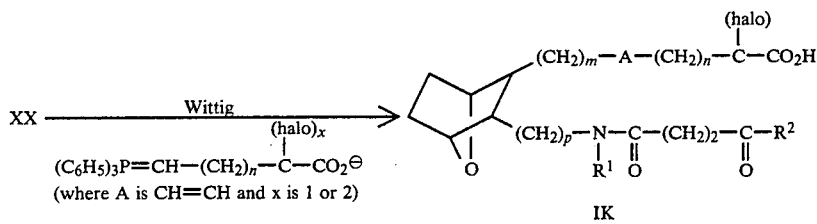

IK

K. Where R is $\overset{O}{\overset{\|}{C}}NR^3R^4$ (wherein $R^3$ and $R^4$ are other than hydroxy or alkoxy)

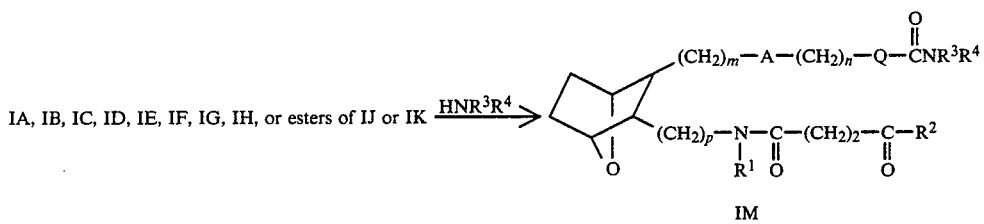

IM

L. Where R is $-\langle\begin{smallmatrix}N=N\\ \| \\ N-N\\ H\end{smallmatrix}$ and A is CH=CH

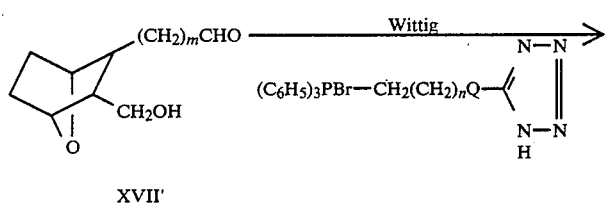

XVII'

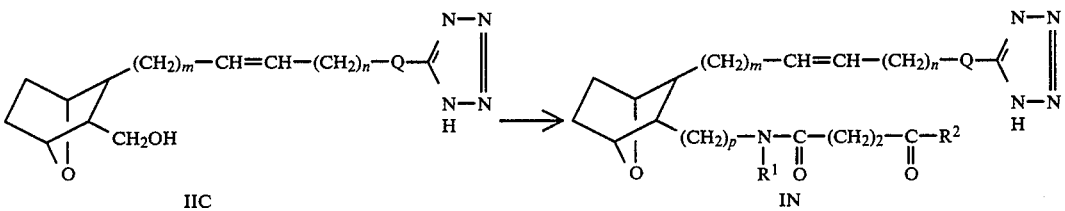

IIC → IN

M. Where R is $-\langle\begin{smallmatrix}N=N\\ \| \\ N-N\\ H\end{smallmatrix}$ and A is $(CH_2)_2$ IN 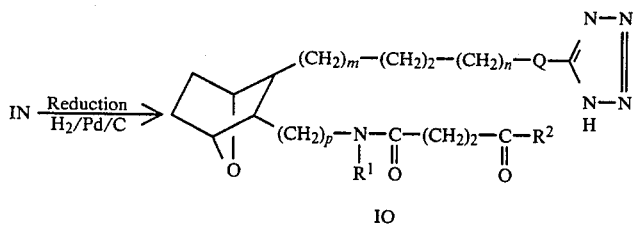 IO N. Where R is CO$_2$H IA to IH 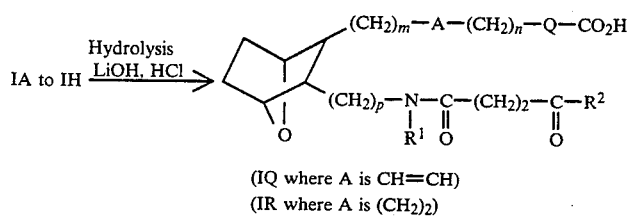

(IQ where A is CH=CH)
(IR where A is (CH$_2$)$_2$)

O. Where R is 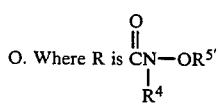

IQ or IR 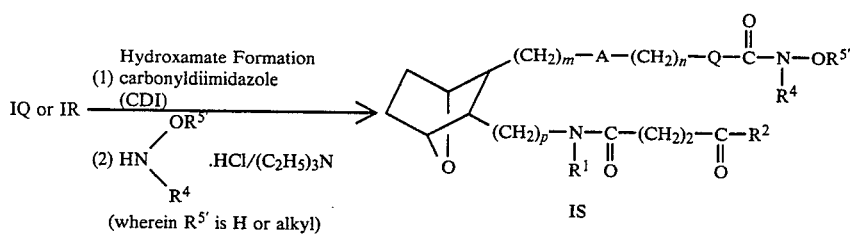 IS (wherein R$^{5'}$ is H or alkyl)

P. 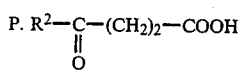

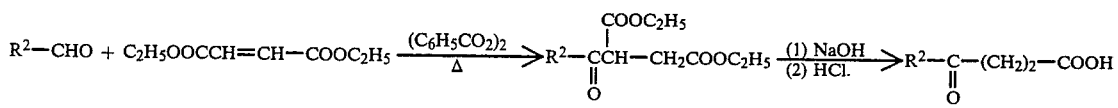

As seen in reaction sequence "A", compounds of the invention where Q is —CH$_2$— or a single bond, p is 1, R is CO$_2$ alkyl, and R$^1$ is H, that is

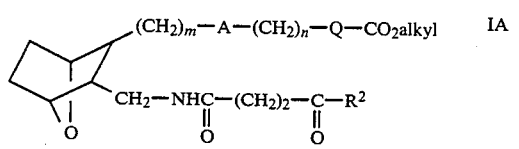 IA are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

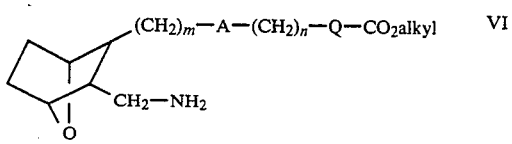 VI

As seen in reaction sequence "A'", where R$^1$ is lower alkyl, an alkylation reaction is carried out as in the reference M. J. O'Donnell et al., *Tetrahedron Lett.* (1984), 25, 3651-3654 to give VIA

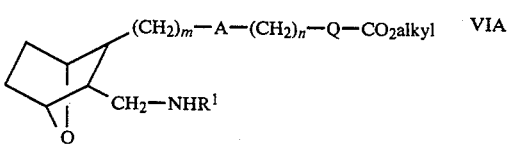 VIA

The amine VI or VIA is then subjected to a CDI coupling reaction by reacting VI or VIA with carbonyldiimidazole and acid compound VII

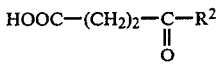

in the presence of an inert organic solvent such as tetrahydrofuran and carbonyldiimidazole (CDI), under an inert atmosphere, such as argon, employing a molar ratio of VI:VII of within the range of from about 1:1 to about 1:3, to form the amide ester compound of the invention IA or IA′

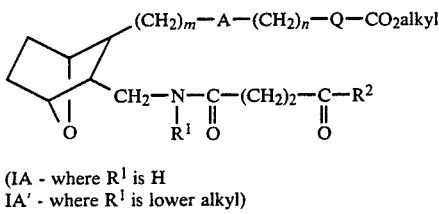

(IA - where $R^1$ is H
IA′ - where $R^1$ is lower alkyl)

The reaction sequences identified as "B" and "B′" are employed to prepare compounds of the invention wherein Q is —$CH_2$— or a single bond, p is 2 to 5, and R is $CO_2$alkyl, that is,

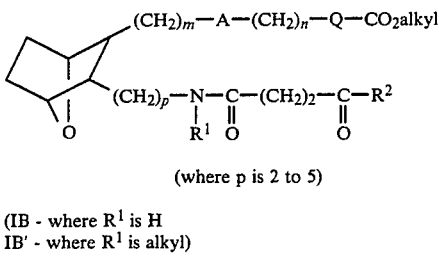

(where p is 2 to 5)

(IB - where $R^1$ is H
IB′ - where $R^1$ is alkyl)

Compound II or IIA is used to form the aldehyde III (where A is —CH=CH—) or IIIA (where A is —$(CH_2)_2$—). Thus, to form aldehyde III where A is —CH=CH—, compound II is subjected to a Collins oxidation, for example, by reacting II with chromium trioxide in pyridine. To form the aldehyde IIIA (where A is —$(CH_2)_2$—) compound II is reduced, for example, with hydrogen over a palladium on carbon catalyst, to form hydroxymethyl compound IIA (where A is $(CH_2)_2$) and compound IIA is subjected to a Collins oxidation to form aldehyde IIIA (where A is $(CH_2)_2$). The aldehyde III or IIIA is used to prepare aldehyde IX (where p is 2-5) by carrying out a homologation sequence, such as a Wittig reaction with $(C_6H_5)_3P$=CHOMe followed by hydrolysis, (p−1) times. The aldehyde IX (where p is 2-5) is then carried on to compounds of this invention where p is 2-5, that is

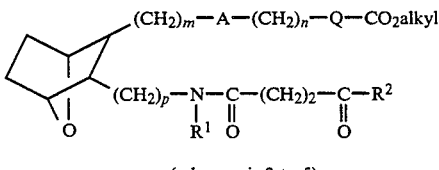

(where p is 2 to 5)

by reducing aldehyde IX by reacting with a reducing agent such as sodium borohydride to form alcohol IXA

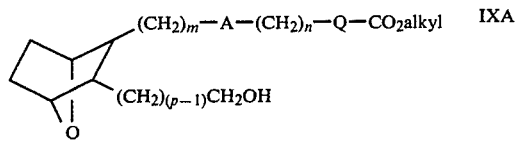

tosylating alcohol IXA as described above to form the tosylate X which is subjected to a displacement reaction with potassium phthalimide as described above to form the phthalimide XI. Phthalimide XI is then made to undergo selective hydrolysis as described above to form the amine XII

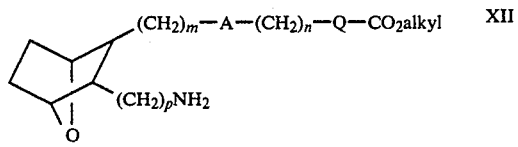

As seen in reaction sequence "B′", where $R^1$ is lower alkyl, an alkylation reaction is carried out as in O'Donnell et al, supra to give XIIA

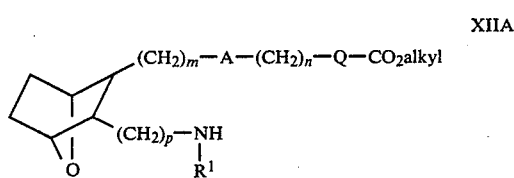

The amine XII or XIIA is then reacted with ketoacid VII as described above to form the amide ester compound of the invention IB or IB′

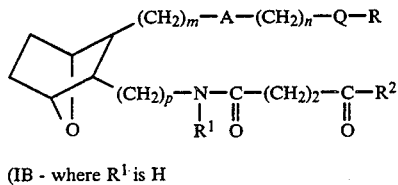

(IB - where $R^1$ is H
IB′ - where $R^1$ is lower alkyl)

Compounds of the invention wherein m is 2, A is —CH=CH—, p is 1 and Q is $CH_2$ or a single bond may be prepared as outlined in reaction sequence "C" by subjecting starting compound XIII to a Wittig reaction, referred to as Wittig (1), by reacting XIII with an alkoxymethyltriphenyl phosphonium halide, such as (methoxymethyl)triphenylphosphonium chloride, for example, as described in Example 4 of U.S. Pat. No. 4,143,054, to form compound F. The Wittig (1) procedure is repeated on compound F to form aldehyde compound XIV. Aldehyde XIV is then subjected to a Wittig (2) procedure wherein XIV is reacted with a carboxyalkyltriphenylphosphonium halide, such as carboxypentyltriphenylphosphonium bromide, to form hydroxymethyl compound XV. Compound XV is esterified, for example, by reacting with diazomethane, to form ester XVI which is then employed in place of compound II in reaction scheme "A" to form compound IC of the invention.

As seen in reaction sequence "D", compounds of the invention wherein m is 2, A is —$CH_2$—$CH_2$—, p is 1 and Q is CH₂ or a single bond may be prepared as outlined in reaction sequence "D" by reducing hydroxymethyl compound XVI to form compound XVIA which is then employed in place of compound IIA in reaction sequence "A" to form compound ID of the invention.

Referring to reaction sequence "E", compounds of the invention wherein m is 3 or 4, A is —CH═CH—, p is 1 and Q is CH₂ or a single bond may be prepared by subjecting aldehyde XIV to the Wittig (1) procedure one time in the case where m is 3 and a second time in the case where m is 4, to form the aldehyde XVII. Aldehyde XVII is then subjected to the Wittig (2) procedure to form acid XVIII which is esterified to form ester XIX which is then employed in place of compound II in reaction scheme "A" to form compound IE of the invention.

As seen in reaction sequence "F", compounds of the invention wherein m is 3 or 4, A is CH₂CH₂, p is 1 and Q is CH₂ or a single bond may be prepared by reducing hydroxymethyl compound XIX to form compound XIXA which is then employed in place of compound II in reaction scheme "A" to form compound IF of the invention.

Thus, compounds of the invention wherein m is 0, 2, 3 or 4 and p is 2, 3 or 4 may be prepared by substituting hydroxymethyl compound XVI, XVIA, XIX, or XIXA in place of hydroxymethyl compound II or IIA in reaction sequences A and B.

Referring now to reaction sequence "G", compounds of the invention wherein m is 0, A is CH═CH, p is 1 and Q is CH₂ or a single bond, that is, compound IG may be prepared by subjecting compound XIII (prepared as described in Example 3 of U.S. Pat. No. 4,143,054) to a Wittig reaction for example, as described in Example 6(c) of U.S. Pat. No. 4,143,054, by reacting XIII with a carboxyalkyltriphenyl phosphonium halide, such as carboxypentyltriphenyl phosphonium bromide to form the hydroxymethyl compound IXV which may then be used to form the ester IG which, in turn, may be hydrolyzed to the corresponding acid.

As seen in reaction sequence "H", where it is desired to prepare compounds of the invention wherein m is 0 and A is (CH₂)₂, the hydroxymethyl compound IXV is reduced by treatment with hydrogen in the presence of a palladium on carbon catalyst to form hydroxymethyl compound IXC which may then be used to form ester IH which then may be hydrolyzed to the corresponding acid.

Referring to reaction sequence "I", compounds of formula I of the invention wherein Q is —CH═CH—, that is IJ

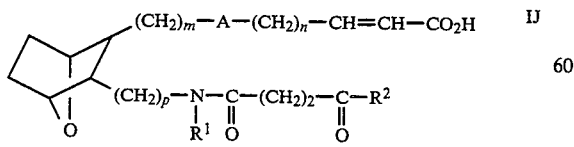

may be prepared by subjecting ester IA, IB, IA', IB', IC, IE and IG to ozonolysis by treating IA, IB, IA', IB', IC, IE and IG with ozone at −78° C. in methylene chloride and methanol to form aldehyde XX.

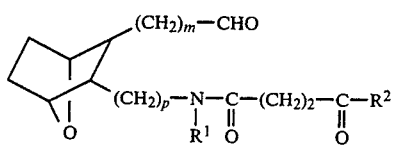

which is then treated with Wittig reagent

(where A is (—CH═CH—))
to form IJ.

In reaction sequence "J" compounds wherein Q is

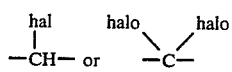

are prepared by subjecting aldehyde XX to a Wittig reaction with

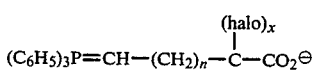

(where A is CH═CH and x is 1 or 2) to form compounds of the invention IK

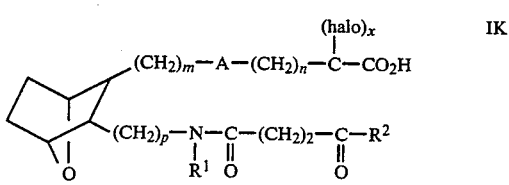

In reaction sequence "K", amides of the invention of structure IM

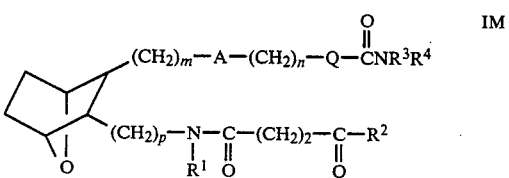

wherein R³ and R⁴ are independently H, alkyl or aryl are prepared by treating ester IA to IH or esters of IJ or IK with an amine of the structure E

HNR³R⁴

Compounds of the invention wherein R is tetrazole 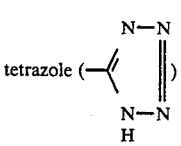

and A is CH═CH are prepared as described in reaction sequence "L" wherein alcohol XVII'

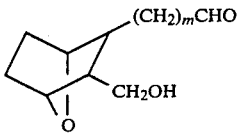

(prepared as described in U.S. Pat. No. 4,143,054) is reacted with a Wittig reagent of the structure G

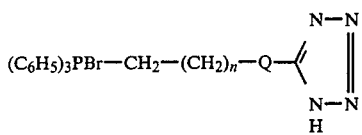

in the presence of a base, such as potassium t-butoxide or sodium hydride-dimethyl sulfoxide employing a molar ratio of XVII:G of within the range of from about 1:1 to about 0.2:1 to form the hydroxymethyl compound IIC

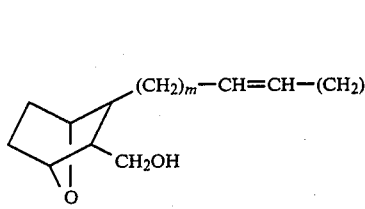

which may then be employed in reaction sequences "A" and "B" in place of compounds II or IIA to form compounds of the invention IN where A is —CH=CH— or IO where A is $(CH_2)_2$

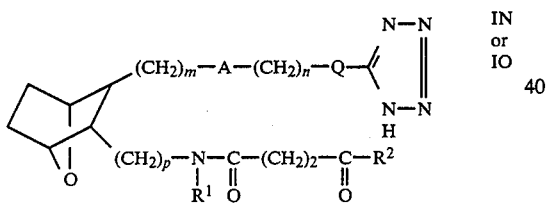

Alternatively, compound IO may be prepared by reducing compound IN by treating with $H_2$ in the presence of palladium on charcoal.

Compounds of the invention wherein R is tetrazole and A is CH=CH may also be prepared by reacting aldehyde XX (disclosed in the reaction sequence "I") with a Wittig reagent of the structure G in the presence of base such as potassium t-butoxide or sodium hydride-dimethyl sulfoxide as described above.

Referring to reaction sequence "N", the esters IA, IA', IB, IB' to IH can be converted to the free acid, that is,

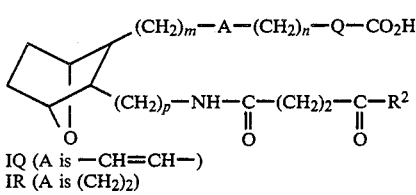

IQ (A is —CH=CH—)
IR (A is $(CH_2)_2$)

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IQ and IR.

In the reaction sequence identified as "O" where in Formula I, R is

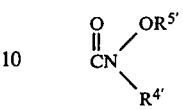

wherein $R^{5'}$ is H or alkyl, a solution of acid IQ or IR dissolved in an inert organic solvent such as tetrahydrofuran (THF) is treated with carbonyldiimidazole (CDI) and the mixture is stirred at room temperature under nitrogen. The resulting active ester is added dropwise into a cold solution of amine hydrochloride H

(wherein $R^{5'}$ is H or alkyl, employing a molar ratio of active ester:H of within the range of from about 0.3:1 to about 1:1 and preferably from about 0.5:1) and triethylamine in tetrahydrofuran to form the hydroxamate IS.

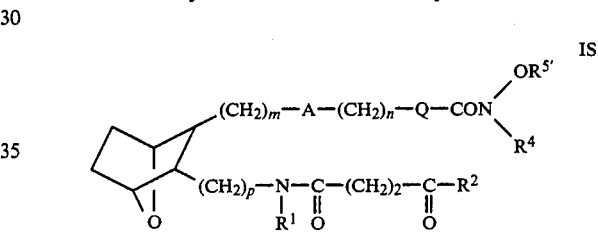

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

As seen in reaction sequence "P", the starting acid VII

and the intermediates are prepared as described in *Organic Synthesis*, Vol. 4, p. 430. The synthesis is as follows. Ethyl maleate and hexanal are reacted to form ethyl hexanoylsuccinate, followed by hydrolysis of esters. The subsequent decarboxylation gives the starting acid VII.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

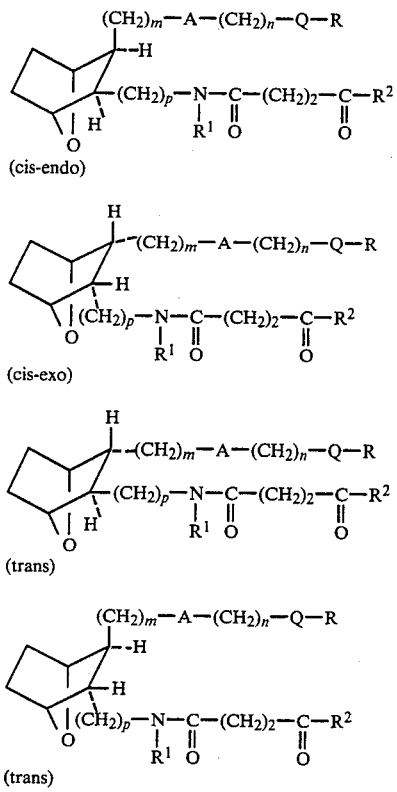

The nucleus in each of the compounds of the invention is depicted as

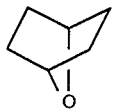

for matter of convenience; it will also be appreciated that the nucleus in the compounds of the invention may be depicted as

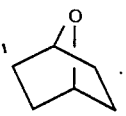

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-[1β,2α(5Z),3α,4β]]-7-[3-[[(1,4-Dioxononyl)amino]methyl]-7-oxabicyclo[2.2.1]hept-2-yl]-5-heptenoic acid, methyl ester A. 4-Oxononanoic acid (a) Ethyl-hexanoylsuccinate n-Hexanal (10 g, 0.1 mole) and ethyl maleate (0.05 mole) were reacted in the presence of benzoyl peroxide (0.1 g) using the procedure described in Organic Synthesis, Vol. 4, p. 430. The title (a) product (4.3 g, 32%) was obtained by distillation, b.p. 112°–114° C./0.3 mm Hg.

(b) 4-Oxononanoic acid

The part (a) ester (1.0 g, 3.7 mmol) was treated with a solution of NaOH (1.5 g, 37.5 mmol) in water (15 ml). The heterogeneous mixture was heated under gentle reflux for 9 hours. After cooling, ether (20 ml) was added. The layers were separated. The aqueous layer was washed with ether (10 ml) and then acidified to pH 2 using concentrated HCl. The product was extracted into ether (3×20 ml). The ether extracts were washed with saturated NaCl solution, dried (MgSO$_4$), and freed of solvent in vacuo leaving an oil which gradually solidified (345 mg). This was crystallized from petroleum ether to give title acid (189.9 mg, 30%) as colorless needles, m.p. 64°–66° C.

B. [1S-[1β,2α(5Z),3α,4β]]-7-[3-(Tosyloxymethyl)-7-oxabicyclo[2.2.1]hept-2-yl]-5-heptenoic acid, methyl ester Tosyl chloride (4.256 g, 22.4 mmol) dissolved in CH$_2$Cl$_2$ (30 ml) was added dropwise to a magnetically stirred solution of [1S-[1β,2α(5Z),3α,4β]]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/H$_2$O and stirred for 30 minutes. The products were extracted with EtOAc (80 ml×3). The combined EtOAc layers were washed with 3N-HCl (40 ml×3), saturated NaHCO$_3$, brine and dried over MgSO$_4$. Filtration and evaporation of solvent gave a white solid, which was crystallized from isopropyl ether to give the corresponding title tosylate in the form of needle crystals (4.23 g, 89%), m.p. 68°–70° C.

C. [1S-[1β,2α(5Z),3α,4β]]-7-[(3-Aminomethyl)-7-oxabicyclo[2.2.1]hept-2-yl]-5-heptenoic acid, methyl ester The title B tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title B tosylate (8.11 g, 19.2 mmol) and purified potassium phthalimide (6.4 g, 34.6 mmol, 18 equiv.) in dimethylsulfoxide (70 ml, Burdick & Jackson) were heated at 90°–100° C. for 2½ hours (checked by TLC Et$_2$O-pet ether 2:1, no tosylate remaining). After cooling to room temperature, water (90 ml) was added. Material began precipitating. The mixture was poured into ice water (~350 ml) and stirred 30 minutes. The straw colored solid was harvested by filtration and washed with more water. The solid was dissolved in warm ethyl acetate (150 ml), washed with water (3×50 ml), dried (MgSO$_4$), filtered and freed of solvent in vacuo. The remaining solid (7.88 g) was recrystallized from isopropyl ether (~150 ml) to give corresponding phthalimide (6.35 g, 83%) TLC. Et$_2$O-hexane 2:1, UV+vanillin R$_f$=0.38, trace 0.09.

The above phthalimide (5.05 g, 13.8 mmol) was dissolved in distilled CH$_2$Cl$_2$ (24 ml) and distilled ethanol (104 ml) in an argon atmosphere. Anhydrous hydrazine (0.78 ml, 25.6 mmol) was added. The mixture was stirred at room temperature. After 8 hours an additional 0.2 ml of hydrazine was added and the mixture was stirred an additional 15 hours at room temperature. A white solid was removed by filtration and washed with more CH$_2$Cl$_2$. The filtrate was taken to dryness in vacuo (on the pump at end). Cold 0.5N HCl solution (80 ml) was added. A small amount of white solid was removed by filtration and washed with additional 0.5N HCl solution (80 ml). The acidic solution was washed with ether (2×100 ml) and then basified with solid K$_2$CO$_3$. The amine was extracted into CHCl$_3$ (3×100 ml), dried (MgSO$_4$) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (2.441 g, 71%). NMR spectra and TLC indicated some minor impurities. The material was used without further purification.

D. [1S-[1β,2α(5Z),3α,4β]]-7-[3-[[(1,4-Dioxononyl)]amino]methyl]-7-oxabicyclo[2.2.1]hept-2-yl]-5-heptenoic acid, methyl ester Part A acid compound (183.6 mg, 1.07 mmol) was dissolved in distilled THF (12 ml) in an argon atmosphere. After cooling in an ice bath carbonyldiimidazole (CDI) (173 mg, 1.07 mmol) was added. The mixture was stirred cold for 1 hour and then at room temperature for 1 hour. The solution was cooled to 0° C. and a solution of Part C amine (283 mg, 1.07 mmol) in THF (3 ml) was added. The mixture was left stirring overnight at room temperature. The solvent was removed in vacuo and the residue was dissolved in CHCl$_3$ (50 ml). This was washed with 1N HCl (20 ml), 1N NaOH (20 ml) and H$_2$O (20 ml), dried (MgSO$_4$) and freed of solvent in vacuo leaving a viscous oil. The oil was chromatographed on silica gel (30 g, Baker for flash chromatography), eluting with 2% methanol in ether to give title compound (305 mg, 67%) which became partially crystalline on standing. TLC: silica gel, 5% MeOH in ether, vanillin R$_f$=0.54. The NMR spectra indicated this contained some impurity.

EXAMPLE 2

[1S-[1β,2α(5Z),3α,4β]]-7-[3-[[(1,4-Dioxononyl)amino]methyl]-7-oxabicyclo[2.2.1]hept-2-yl]-5-heptenoic acid The Example 1 methyl ester (302 mg, 0.716 mmol) was dissolved in distilled THF (40 ml) and water (8 ml) in an argon atmosphere. 1N LiOH solution (9.5 ml) was added and the mixture was stirred at room temperature for 3¾ hours. After neutralization with 1N HCl (9.5 ml), solid KCl was added and the layers were separated. The aqueous layer was reextracted with CHCl$_3$ (3×50 ml). The combined organic layers (THF+CHCl$_3$) were washed with saturated NaCl solution (2×25 ml), dried (MgSO$_4$), and freed of solvent in vacuo leaving 253 mg of oil. This was chromatographed on silica gel (20 g, Baker for flash chromatography) eluting with 2% MeOH in EtOAc to give a white solid (107 mg, 36%). This was recrystallized from EtOAc-ether to give title acid, 56 mg, 19%, m.p. 81°–83° C.) [α]$_D$=−6.1% (c=1.1, MeOH). TLC: silica gel, 5% MeOH in EtOAc, vanillin, R$_f$=0.37.

Anal Calcd for C$_{22}$H$_{36}$O$_5$N: C, 67.78; H, 8.15; N, 3.44; Found: C, 64.87; H, 9.27; N, 3.48.

EXAMPLE 3

[1S-[1β,2α(5Z),3α,4β]]-7-[3-[[(1-4-Dioxodecyl)amino]methyl]-7-oxabicyclo[2.2.1]hept-2-2-yl]-5-heptenoic acid, methyl ester

A. 4-Oxodecanoic acid

Following the procedure of Example 1 Part A except substituting n-heptanal for n-hexanal, the title compound is obtained.

B. [1S-[1β,2α(5Z),3α,4β]]-7-[3-[[(1,4-Dioxodecyl)amino]methyl]-7-oxabicyclo[2.2.1]hept-2-yl]-5-heptenoic acid, methyl ester Following the procedure set out in Example 1 Part D, except substituting the title A acid for the Example 1 Part A acid, the title compound is obtained.

EXAMPLE 4

[1S-[1β,2α(5Z),3α,4β]]-7-[3-[[(1,4-Dioxodecyl)amino]methyl]-7-oxabicyclo[2.2.1]hept-2-yl]-5-heptenoic acid Following the procedure of Example 2 except substituting the Example 3 ester for the Example 1 ester, the title compound is obtained.

EXAMPLE 5

[1S-[1β,2α(5Z),3α,4β]]-2,2-Difluoro-7-[3-[[(1,4-dioxononyl)amino]methyl]-7-oxabicyclo[2.2.1]hept-2-yl]-5-heptenoic acid

A.

[1S-[1β,2α,3α,4β]]-2-[3-[[(1,4-dioxononyl)amino]methyl]-7-oxabicyclo[2.2.1]-hept-2-yl]acetaldehyde $O_3$ is bubbled through a magnetically stirred solution of [1S-[1β,2α(5Z), 3α,4β]]-7-[3-[[(1,4-dioxononyl)amino]methyl]-7-oxa-bicyclo[2.2.1]hept-2-yl]-5-heptenoic acid, methyl ester (203.5 mg, 0.5 mmol) (prepared as described in Example 1) in $CH_2Cl_2$/MeOH (10 ml/10 ml) at −78° C., until the solution becomes blue. Excess $O_3$ is then purged by a stream of $N_2$ and $(CH_3)_2S$ (1 ml) is added. The reaction is allowed to warm to room temperature and poured into $CH_2Cl_2$ (50 ml), $H_2O$ (10 ml). The products are extracted into $CH_2Cl_2$ layers. The $H_2O$ layer separated is re-extracted with $CH_2Cl_2$ (30 ml). The combined $CH_2Cl_2$ layers are washed with brine (10 ml) and dried over $MgSO_4$. Filtration and evaporation of solvent gives a crude product which is purified by silica gel column chromatography to afford the title compound.

B. (4-Carboxy-3,3-difluorobutyl)triphenylphosphonium bromide (1) Methyl tetrahydrofuroate Methyl furoate (75 g, 0.595 mole) was dissolved in MeOH (150 ml), and poured into a Parr bottle. Air was replaced with argon, and then 10% Pd/C (2.5 g) was added. The atmosphere was replaced with $H_2$ and methyl furoate was hydrogenated at 40 psi for 48 hours. The reaction was filtered through celite pad, and the pad was washed with ether. The filtrate and the wash were combined and distilled to give the title compound (71 g, 0.546 mole, 59° C./5.1 mmHg, 92%) as a colorless liquid.

(2) Methyl 2-acetoxy-5-bromopentanoate

HBr gas was bubbled into $Ac_2O$ (200 ml) at 0° C. for 2 hours. The specific gravity became 1.4. Part 1) methyl tetrahydrofuroate (70 g, 0.538 mole) was added dropwise under magnetic stirring at 0° C. and the reaction was allowed to warm to room temperature. After stirring overnight, the reaction was poured into ice (~1200 ml) carefully, and left for 30 minutes with occasional swirling. The products were extracted with $Et_2O$ (600 ml×2 and 300 ml). The combined $Et_2O$ layers were washed with dilute NaOH (~0.5%) solution, until the wash became basic. The $Et_2O$ layer was further washed with $H_2O$, dried over $Na_2SO_4$, and filtered. The filtrate was concentrated and distilled to give the title compound (116 g, 0.458 mole, 108° C./1 mmHg, 85%) as a colorless liquid.

(3) Methyl 5-bromo-2-hydroxypentanoate

MeOH (100 ml, distilled over $Mg(OMe)_2$) was saturated with HBr gas at 0° C. This was added to Part 2) compound (60 g, 0.237 mole) in MeOH (200 ml distilled over $Mg(OMe)_2$). The reaction was allowed to warm to room temperature and stirred overnight. The reaction was concentrated in vacuo. Toluene (200 ml) was added to the resulting liquid, and the reaction was concentrated. The same process was repeated twice. The resulting liquid was dissolved in EtOAc (2000 ml) and washed with 0.5% NaOH, brine, and dried over $MgSO_4$. Filtration and evaporation of solvent gave a straw colored oil (44.8 g). This was distilled to give the title compound (34 g, 0.161 mole, 68%) as a colorless liquid.

(4) Methyl 5-bromo-2-oxopentanoate

Jones' reagent ($CrO_3$: 9.58 g, $H_2SO_4$: 8.47 ml, $H_2O$: 36.8 ml) was added to a magnetically stirred solution of Part (3) compound (12.53 g, 59.3 mmole) in acetone (150 ml) at room temperature. The addition was controlled to maintain the temperature below 35° C. After the completion of the addition, the reaction was stirred at room temperature for 45 minutes. Isopropyl alcohol (30 ml) was added dropwise and stirred for 30 minutes. The reaction was then diluted with $H_2O$ (500 ml) and the products were extracted with $CH_2Cl_2$ (1 l.). The $CH_2Cl_2$ layer was washed with brine (100 ml×3) and dried over $MgSO_4$. Filtration and evaporation of solvents gave the title compound (11.4 g, 54.5 mmole, 92%) as a colorless liquid.

(5) Methyl 5-bromo-2,2-difluoropentanoate

Part (4) compound (11.4 g, 54.5 mmole) was added dropwise to $(C_2H_5)_2$ $NSF_3$ (DAST) (6.8 ml, 55.7 mmole) at room temperature. The container of Part (4) was rinsed with $CH_2Cl_2$ (20 ml), which was added to the reaction. The reaction was stirred at room temperature for 1 hour and poured into $H_2O$ (80 ml). The products were extracted with $CH_2Cl_2$ (40 ml×3). The combined $CH_2Cl_2$ layers were washed with $H_2O$ (20 ml×3) and dried over $MgSO_4$. Filtration and evaporation of solvent gave a straw colored liquid (10.8 g). This was distilled to give the title compound (8.4 g, 36.3 mmole, 67%, 41° C./0.015 mmHg) as a colorless liquid.

(6) 5-Bromo-2,2-difluoropentanoic acid

HBr gas was introduced into 48% HBr in $H_2O$ (100 ml) with occasional cooling in an ice bath until the weight became 180 g. The HBr solution was then added to Part (5) compound (8.4 g, 36.3 mmole) at room temperature and the reaction was stirred for 5 hours at room temperature. The reaction was cooled to 0° C. and poured into $Et_2O$ (900 ml) in an ice bath. The products were extracted into the $Et_2O$ layer. The water layer was further extracted with $Et_2O$ (200 ml and 100 ml). The combined ether layers were washed with $H_2O$ (200 ml). The $H_2O$ wash was backwashed with $Et_2O$ (100 ml). The $Et_2O$ layers were combined and dried over $MgSO_4$. Filtration and evaporation of solvent gave the title compound (7.8 g, quant.) as a colorless liquid.

(7) (4-Carboxy-3,3-difluorobutyl)triphenylphosphonium bromide

Acetonitrile (23 ml) was added to a mixture of triphenylphosphine (6.7 g, 25.7 mmole) and Part (6) compound (4.6 g, 21.2 mmole). The solution was heated at gentle reflux under magnetic stirring for 30 hours. Toluene (46 ml) was then added and the reaction was brought to reflux for a brief period. The reaction was allowed to cool to 5° C. and kept overnight. The resulting white precipitates were collected, washed with cold acetonitrile/toluene (½), and dried in a heated vacuum oven (60° C. ~5 mmHg) to give the title bromide (9.8 g, 20.4 mmole, 96.5%) as white solid.

C.

[1S-[1β,2α(5Z),3α,4β]]-2,2-Difluoro-7-[3-[[(1,4-dioxononyl)amino]methyl]-7-oxabicyclo[2.2.1]hept-2-yl]-5-heptenoic acid (4-Carboxy-3,3-difluorobutyl)triphenylphosphonium bromide (1.27 g) (prepared in Part B) is suspended in THF (15 ml). KOt-Amylate (1.7M in toluene, 3 ml) is added at room temperature. The reaction is stirred for 4 hours. The resulting solution is transferred dropwise to aldehyde obtained in Part A, (531 mg) in THF (10 ml) at 0° C. The reaction is warmed to room temperature and stirred for 15 hours. Saturated NH4Cl (25 ml) is added and the products are extracted with EtOAc (40 ml×3). The combined organic layers are washed with brine (30 ml) and dried over MgSO4. Filtration and evaporation of solvents afford a crude product, which is purified by silica gel column to give the title compound.

EXAMPLE 6

[1S-[1β,2α(2E,5Z),3α,4β]]-7-[3-[[(1,4-Dioxononyl)amino]methyl]-7-oxabicyclo[2.2.1]hept-2-yl]-2,5-heptadienoic acid (4-Carboxy-2-butenyl)triphenylphosphonium bromide (1.13 g) is suspended in THF (15 ml). KOt Amylate (1.7M in toluene, 3 ml) is added at room temperature. The reaction is stirred for 4 hours. The resulting solution is transferred dropwise to aldehyde obtained in Example 5 Part A, (530 mg) in THF (10 ml) at 0° C. The reaction is warmed to room temperature and stirred for 15 hours. Saturated NH4Cl (25 ml) is added and the products are extracted with EtOAc (40 ml×3). The combined organic layers are washed with brine (30 ml) and dried over MgSO4. Filtration and evaporation of solvents afford a crude product, which is purified by silica gel column to give the title compound.

EXAMPLE 7

[1S-[1β,2α(5Z),3α,4β]]-N-Methyl-7-[3-[[(1,4-dioxononyl)amino]methyl]-7-oxabicyclo[2.2.1]hept-2-yl]-5-heptenamide 40% MeNH2 in H2O (2 ml) is added to a magnetically stirred solution of ester prepared in Example 1 (205 mg) in THF (14 ml) at room temperature. Stirring is continued overnight (17 hours) at room temperature. The reaction is concentrated in vacuo to give a crude product which is purified by silica gel column. The title compound is then obtained.

EXAMPLE 8

[1S-(1β,2α,3α,4β)]-7-[3-[[(1,4-Dioxononyl)amino]methyl]-7-oxabicyclo[2.2.1]hept-2-yl]heptanoic acid

A.

[1S-(1β,2α,3α,4β)]-7-[3-(Hydroxymethyl)-7-oxabicyclo[2.2.1]hept-2-yl]heptanoic acid, methyl ester To 800 mg (3.0 mmole) of the [1S-[1β,2α(Z),3α,4β]]-7-[3-(hydroxymethyl)-7-oxabicyclo[2.2.1]hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

[1S-(1β,2α,3α,4β)]-7-[3-[[(1,4-Dioxononyl)amino]methyl]-7-oxabicyclo[2.2.1]hept-2-yl]heptanoic acid Following the procedure of Examples 1 and 2 except substituting the Part A alcohol-ester for the alcohol ester employing in Example 1 Part B, the title product is obtained.

EXAMPLE 9

[1S-[1β,2α(5Z),3α,4β]]-7-[3-[[(1,4-Dioxohexyl)amino]methyl]-7-oxabicyclo[2.2.1]hept-2-yl]-5-heptenoic acid Following the procedure of Examples 1 and 2 except substituting 4-oxohexanoic acid for the Example 1 Part A acid, the title compound is obtained.

EXAMPLE 10

[1S-[1β,2α(5Z),3α,4β]]-7-[3-[[(4-Cyclohexyl-1,4-dioxobutyl)amino]methyl]-7-oxabicyclo[2.2.1]hept-2-yl]-5-heptenoic acid Following the procedure of Examples 1 and 2 except substituting 4-cyclohexyl-4-oxobutanoic acid for the Example 1 Part A acid, the title compound is obtained.

EXAMPLE 11

[1S-[1β,2α(5Z),3α,4β]]-7-[3-[[(1,4-Dioxo-6-octenyl)amino]methyl]-7-oxabicyclo[2.2.1]hept-2-yl]-5-heptenoic acid Following the procedure of Examples 1 and 2 except substituting 4-oxo-6-octenoic acid for the Example 1 Part A acid, the title compound is obtained.

EXAMPLE 12

[1S-[1β,2α(5Z),3α,4β]]-7-[3-[[(1,4-Dioxo-5-phenylpentyl)amino]methyl]-7-oxabicyclo[2.2.1]hept-2-yl]-5-heptenoic acid Following the procedure of Examples 1 and 2 except substituting 4-oxo-5-phenylpentanoic acid for the Example 1 Part A acid, the title compound is obtained.

EXAMPLE 13

[1S-[1β,2α(5Z),3α,4β]]-7-[3-[[[(1,4-Dioxo-4-phenylbutyl)amino]methyl]-7-oxabicyclo[2.2.1]hept-2-yl]-5-heptenoic acid Following the proecedure of Examples 1 and 2 except substituting 4-oxo-4-phenylbutanoic acid for the Example 1 Part A acid, the title compound is obtained.
Example 1 Part A acid, the title compound is obtained.

EXAMPLE 14

[1S-[1β,2α(5Z),3α,4β]]-7-[3-[2-[[(1,4-Dioxononyl)amino]ethyl]-7-oxabicyclo[2.2.1]hept-2-yl]-5-heptenoic acid

A.

[1S-[1β,2α(Z),3α,4β]]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride ((C6H5)3P+-CH2OCH3Cl−) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1S-[1β,2α(5Z),3α,4β]]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH4Cl, and extracted with ether (4×200 ml). The combined ether phases were washed with NaCl, saturated solution, and dried (MgSO4) and concentrated to yield a yellow oil in a white crystalline solid (phosphine oxide). The white solid was triturated with EtOAc and the mother liquor was purified by chromatography on an LPS-1 silica column. The fractions obtained were (A) [1S-[1β,2α(Z),3α,4β]]-7-[3-(2-oxo)ethyl-7-oxabicyclo[2.2.1-]hept-2-yl]-5-heptenoic acid, methyl ester, (B) [1S-[1β,2α(Z),3α,4β]]-7-[3-(2-methoxy)ethenyl-7-oxabicyclo[2.2.1]hept-2-yl]-5-heptenoic acid, methyl ester, and (C) [1S-[1β,2α(Z),3α,4β]]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1S-[1β,2α(5Z),3α,4β]]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH4 (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO3, saturated NaCl and dried (MgSO4). The ether is evaporated to yield the title B compound.

C.

[1S-[1β,2α(Z),3α,4β]]-7-[3-[2-[[(1,4-Dioxononyl)amino]ethyl]-7-oxabicyclo[2.2.1]hept-2-yl]-5-heptenoic acid Following the procedure of Examples 1 and 2 except substituting the above part B alcohol for the alcohol used in Example 1 Part B, the title compound is obtained.

EXAMPLE 15

[1S-(1β,2α,3α,4β)]-7-[3-[2-[[(1,4-Dioxononyl)amino]ethyl]-7-oxabicyclo[2.2.1]hept-2-yl]heptanoic acid Following the procedure of Examples 14 and 1 except substituting [1S-(1β,2α,3α,4β)]-7-[3-formyl-7-oxabicyclo[2.2.1]hept-2-yl]heptanoic acid, methyl ester for [1S-[1β,2α(Z),3α,4β]]-7-[3-formyl-7-oxabicyclo[2.2.1]hept-2-yl]-5-heptenoic acid, methyl ester, the title compound is obtained.

EXAMPLE 16

[1S-[1β,2α(5Z),3α,4β]]-7-[3-[4-[(1,4-Dioxononyl)amino]butyl]-7-oxabicyclo[2.2.1]hept-2-yl]-5-heptenoic acid

A.

[1S-[1β,2α(5Z),3α,4β]]-7-[3-(3-Oxo)propyl-7-oxabicyclo[2.2.1]hept-2-yl]-5-heptenoic acid, methyl ester Following the procedure of Example 14 Part A except substituting [1S-[1β,2α(Z),3α,4β]]-7-[3-(2-oxo)ethyl-7-oxabicyclo[2.2.1]hept-2-yl]-5-heptenoic acid, methyl ester for [1S-[1β,2α(Z),3α,4β]]-7-[3-formyl-7-oxabicyclo[2.2.1]hept-2-yl]-5-heptenoic acid, methyl ester, the title A compound is obtained.

B.

[1S-[1β,2α(Z),3α,4β]]-7-[3-(4-Oxo)butyl-7-oxabicyclo[2.2.1]hept-2-yl]-5-heptenoic acid, methyl ester Following the procedure of Example 14 Part A except substituting the aldehyde from Part A above for [1S-[1β,2α(Z),3α,4β]]-7-[3-formyl-7-oxabicyclo[2.2.1-]hept-2-yl]-5-heptenoic acid, methyl ester, the title B compound is obtained.

C.

[1S-[1β,2α(Z),3α,4β]]-7-[3-(4-Hydroxybutyl)-7-oxabicyclo[2.2.1]hept-2-yl]-5-heptenoic acid, methyl ester Following the procedure of Example 14 Part B except substituting the title B aldehyde for [1S-[1β,2α(Z),3α,4β]]-7-[3-(2-oxo)ethyl-7-oxabicyclo[2.2.1]hept-2-yl]-5-heptenoic acid, methyl ester, the title C alcohol is obtained.

D.

[1S-[1β,2α(Z),3α,4β]]-7-[3-[4-[(1,4-Dioxononyl)amino]butyl]-7-oxabicyclo[2.2.1]hept-2-yl]-5-heptenoic acid Following the procedure of Examples 1 and 2 except substituting the above Part C alcohol for the alcohol used in Example 1, the title compound is obtained.

EXAMPLE 17

[1S-[1β,2α(5Z),3α,4β]]-8-[3-[[(1,4-Dioxononyl)amino]methyl]-7-oxabicyclo[2.2.1]hept-2-yl]-5-octenoic acid

A.

[1S-(1β,2α,3α,4β)]-3-[3-(Hydroxymethyl)-7-oxabicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4M potassium t-amylate in toluene (1910 ml, 2.67 mol) over 20 minutes. The resultant dark red solution was stirred at 0° C. for 1 hour. The mixture was then treated slowly over 5 minutes with solid hemiacetal (XIII in reaction sequence C) prepared as described in Example 3 of U.S. Pat. No. 4,143,054 (200 g, 1.28 mol). The temperature gradually rose to 23° C. The mixture was stirred vigorously at room temperature for 90 minutes. The reaction mixture was then chilled to 0° C. and treated slowly with acetaldehyde (124 ml, 2.2 mol) over 10 minutes. The mixture was diluted with water (2500 ml) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for 90 minutes then filtered. The solids were washed thoroughly with isopropyl ether. The filtrate was concentrated in vacuo to an oily residue (460 g). This oily residue was treated with water (4000 ml) and stirred vigorously for 2 hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 ml). The mixture was then stirred at room temperature for 3 hours. After this time the solution was neutralized by the slow addition of solid sodium bicarbonate (720 g). The mixture was filtered through a bed of Celite then extracted with hexane (4×2 liters) then ethyl acetate (10×2 liters). The combined ethyl acetate extracts were dried over MgSO$_4$ and concentrated in vacuo. The solid residue was triturated with hexane (1 liter), filtered, and dried in vacuo to yield 220 g (100%) of desired compound (hemiacetal F in reaction sequence C), m.p. 104°–105° C., $[\alpha]_D = +27°$ c=1 MeOH.

TLC: Silica gel; EtOAc; R$_f$=0.3; Ce(SO$_4$)$_2$.

The above Wittig procedure was repeated on the hemiacetal F used in place of hemiacetal XIII to form the title aldehyde.

B.
[1S-[1β,2α(Z),3α,4β]]-8-[3-(Hydroxymethyl)-7-oxabicyclo[2.2.1]hept-2-yl]-5-octenoic acid, methyl ester A Wittig reagent was prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of Part A aldehyde 1.02 g (6 mmole) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 70 g of silica gel with 50/50 ethyl acetate-hexane as the eluant which gave 1.1 g of acid. This was treated with diazomethane (CH$_2$N$_2$) in Et$_2$O to give the title compound.

C.
[1S-[1β,2α(Z),3α,4β]]-8-[3-[[(1,4-Dioxononyl)amino]methyl]-7-oxabicyclo[2.2.1]hept-2-yl]-5-octenoic acid Following the procedure of Examples 1 and 2 except substituting the title B ester for the ester used in Example 1 Part B, the title compound is obtained.

EXAMPLE 18
[1S-[1β,2α(Z),3α,4β]]-6-[3-[[(1,4-Dioxononyl)amino]methyl]-7-oxabicyclo[2.2.1]hept-2-yl]-1-(1H-tetrazol-5-yl)-4-hexene

A.
[1S-[1β,2α(Z),3α,4β]]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO$_3$ solution, washed with 100 ml of ether, acidified with dilute HCl to pH 3, and extracted with three 500 ml portions of ethyl acetate. The combined organic solutions are dried over anhydrous MgSO$_4$, and purified by silica chromatography using a 5% methanol in methylene chloride eluant to provide 2 g of title A compound.

B.
[1S-[1β,2α(5Z),3α,4β]]-6-[3-[[(1,4-Dioxononyl)amino]methyl]-7-oxabicyclo[2.2.1]hept-2-yl]-1-(1H-tetrazol-5-yl)-4-hexene Following the procedure of Examples 1 and 2 except substituting the Part A compound for the hydroxymethyl compound used in Example 1 Part B, the title compound is obtained.

EXAMPLE 19
[1S-[1β,2α(5Z),3α,4β]]-7-[3-[[(1,4-Dioxononyl)amino]methyl]-7-oxabicyclo[2.2.1]hept-2-yl]-N-hydroxy-N-methyl-5-heptenamide A solution of Example 2 acid (0.82 mmole) in dry tetrahydrofuran (5.0 ml) is treated with carbonyldiimidazole (CDI) (0.82 mmole) at 0° C. and stirred at 0° for 1 hour and at room temperature for 1 hour. The reaction is added dropwise into a cold solution (0°, ice-water) of 98% methylhydroxylamine hydrochloride (139.8 mg; 1.64 mmole; 2 eq.) and triethylamine (0.34 ml; 2.46 mmole; 3 eq.) in tetrahydrofuran (2 ml). The mixture is stirred at 0° under nitrogen for 30 minutes and at room temperature overnight, diluted with water (10 ml) and extracted twice with dichloromethane (50 ml). The organic extract is washed with 1N HCl (10 ml), 5% NaHCO$_3$ (5 ml) and water (10 ml), dried (anhydrous MgSO$_4$), filtered and evaporated to dryness giving the crude product, which is purified by silica gel column to afford the title compound.

EXAMPLE 20
[1S-[1β,2α(6Z),3α,4β]]-7-[3-[[(1,4-Dioxononyl)amino]methyl]-7-oxabicyclo[2.2.1]hept-2-yl]-6-heptenoic acid

A.
[1S-[1β,2α(6Z),3α,4β]]-7-[3-(Hydroxymethyl)-7-oxabicyclo[2.2.1]hept-2-yl]heptenoic acid, methyl ester A slurry of carboxypentyl triphenylphosphonium bromide in THF is cooled in an ice bath and treated dropwise with 1.4M KOt-amylate in toluene. After completion of this addition, the reaction mixture is allowed to warm to room temperature and is stirred for 6 hours. To this stirred solution is then added a solution of hemiacetal XIII (reaction sequence G) (prepared as described in Example 3 of U.S. Pat. No. 4,143,054) in THF dropwise over 30 minutes. The reaction mixture is then stirred overnight (15 hours). The mixture is cooled in an ice bath and quenched with HOAc. The solvent is removed in vacuo and the resulting residue is dissolved in saturated NaCl solution. This is extracted with chloroform. The chloroform layers are then extracted with saturated NaHCO₃ solution. The aqueous extracts are acidified to pH~3.5 by addition of aqueous HCl solution, and then are extracted with several portions of chloroform. The combined chloroform extracts are concentrated in vacuo to afford the crude product. The crude acid is esterified with excess ethereal diazomethane at 0° C. and then is purified by chromatography on silica gel to afford the title ester.

B. [1S-[1β,2α(6Z), 3α,4β]]-7-[3-[[(1,4-Dioxononyl)amino]methyl]-7-oxabicyclo[2.2.1]hept-2-yl]-6-heptenoic acid Following the procedure of Examples 1 and 2 except substituting the Part A ester for the hydroxymethyl compound used in Example 1 Part B, the title compound is obtained.

EXAMPLE 21

[1S-[1β,2α(2E),3α,4β]]-7-[3-[[(1,4-Dioxononyl)amino]methyl]-7-oxabicyclo[2.2.1]hept-2-yl]-2-heptenoic acid

A. [1S-(1β,2α,3α,4β)]-5-[3-(Hydroxymethyl)-7-oxabicyclo[2.2.1]hept-2-yl]pentanal Following the procedure of Example 17 Part A, except substituting [1S-(1β,2α,3α, 4β)]-3-[3-(hydroxymethyl)-7-oxabicyclo[2.2.1]hept-2-yl]propionaldehyde for the hemiacetal XIII (see reaction sequence C or E), [1S-(1β,2α,3α,4β)]-4-[3-(hydroxymethyl)-7-oxabicyclo[2.2.1]hept-2-yl]butanal is obtained. Then by repeating the procedure of Example 17 Part A on [1S-(1β,2α,3α,4β)]-4-[3-(hydroxymethyl)-7-oxabicyclo[2.2.1]hept-2-yl]butanal, the title A aldehyde is produced.

B. [1S-[1β,2α(2E),3α,4β]]-7-[3-(Hydroxymethyl)-7-oxabicyclo[2.2.1]hept-2-yl]-2-heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title ester.

C. [1S-[1β,2α(2E),3α,4β]]-7-[3-[[(1,4-Dioxononyl)amino]methyl]-7-oxabicyclo[2.2.1]hept-2-yl]-2-heptenoic acid Following the procedure of Example 1 except substituting the Part B ester for the ester used in Example 1 Part B, the title compound is obtained.

EXAMPLE 22

[1S-[1β,2α(5Z),3α,4β]]-7-[3-[(Methylamino)methyl]-7-oxabicyclo[2.2.1]hept-2-yl]-5-heptenoic acid, methyl ester Chiral amine from Example 1, Part C, (1 mmole) and N,N-dimethylformamide dimethylacetal (1.5 mmole) are dissolved in CH₂Cl₂ (6 ml). The reaction is stirred at room temperature overnight. The solvent and the excess reagent are evaporated to give crude amidine, which is dissolved in CH₂Cl₂ (5 ml). Methyl triflate (2 mmole) is added into the reaction at room temperature and the reaction is stirred for 1 hour at room temperature. The organic solvent and the excess reagent are evaporated off in vacuo and the residue is treated with methanolic hydrogen chloride at room temperature overnight. The reaction is concentrated in vacuo and the resulting crude product is dissolved in 1N HCl. The water layer is washed with ethyl ether and basified with saturated NaHCO₃. The water layer is extracted with ethyl ether, which is dried over MgSO₄. Filtration and evaporation of the solvent leave a crude product, which is purified by silica gel column to give the title compound.

The title compound is then employed in place of the chiral amine from Example 1 Part C to prepare compounds of the invention wherein R¹ is CH₃.

EXAMPLES 23 TO 50

Following the procedures outlined in the specification and described in the above working Examples, the following compounds may be prepared.

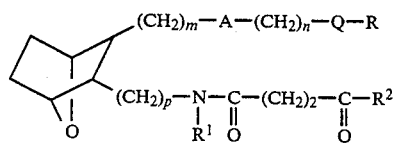

| Ex. No. | m | A | (CH₂)ₙ | Q | R | p | R¹ | R² |
|---|---|---|---|---|---|---|---|---|
| 23. | 2 | CH=CH | CH₂ | CH=CH | CO₂H | 1 | H | H |
| 24. | 3 | (CH₂)₂ | (CH₂)₂ | CH₂ | CO₂H | 2 | C₂H₅ | CH₃ |
| 25. | 4 | CH=CH | (CH₂)₃ | —CH₂— |  | 3 | CH₃ | —CH₂CH=CH—CH₃ |
| 26. | 1 | (CH₂)₂ | (CH₂)₄ |  |  | 1 | CH₃ | 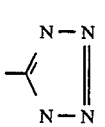 |

-continued

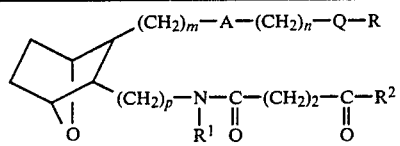

| Ex. No. | m | A | (CH₂)ₙ | Q | R | p | R¹ | R² |
|---|---|---|---|---|---|---|---|---|
| 27. | 0 | CH=CH | (CH₂)₅ | -C(F)(F)- | $\underset{\underset{CH_3}{|}}{\overset{O}{\overset{\|}{C}}}N-OH$ | 2 | H | -CH₂-cyclopentyl |
| 28. | 2 | CH=CH | -CH(CH₃)- | CH=CH | $\underset{H}{\overset{O}{\overset{\|}{C}}}N-OCH_3$ | 3 | C₂H₅ | -CH₂-CH=CH-CH₃ (cis) |
| 29. | 3 | (CH₂)₂ | -C(CH₃)₂- | CH₂ | $\underset{CH_3}{\overset{O}{\overset{\|}{C}}}N-OC_2H_5$ | 4 | H | C₆H₅ |
| 30. | 4 | (CH₂)₂ | (CH₂)₄ | -CH₂- | $\overset{O}{\overset{\|}{C}}NHC_6H_5$ | 1 | C₃H₇ | C₆H₅ |
| 31. | 1 | CH=CH | -C(CH₃)(CH₃)-CH₂- | -CH(F)- | CO₂Li | 2 | H | CH₂C₆H₅ |
| 32. | 0 | CH=CH | -CH(CH₃)-CH(CH₃)- | -C(F)(F)- | CO₂Na | 3 | CH₃ | -(CH₂)₂C₆H₅ |
| 33. | 1 | (CH₂)₂ | -C(CH₃)(F)-CH₂- | CH=CH | CO₂glucamine salt | 4 | C₂H₅ | -C₆H₄-p-CH₃ |
| 34. | 2 | CH=CH | -CH(F)-CH(F)- | CH₂ | CO₂tris salt | 1 | H | -C₆H₄-p-OH |
| 35. | 3 | (CH₂)₂ | -C(F)(F)-CH₂- | -C(F)(F)- | CO₂H | 2 | C₄H₉ | -cyclopentyl |
| 36. | 4 | (CH₂)₂ | -(CH₂)₅ | -CH(F)- | tetrazole (N-N / N-N-H) | 3 | H | -CH₂-cyclobutyl |
| 37. | 0 | CH=CH | -CH₂-CH(CH₃)-CH₂- | -C(F)(F)- | $\overset{O}{\overset{\|}{C}}NH_2$ | 4 | CH₂ | -CH₂-cyclohexyl |
| 38. | 0 | (CH₂)₂ | -CH₂-C(CH₃)(CH₃)- | — | $\underset{H}{\overset{O}{\overset{\|}{C}}}NOH$ | 1 | C₂H₅ | -C₆H₅ |
| 39. | 1 | CH=CH | CH₂ | — | $\overset{O}{\overset{\|}{C}}N(CH_3)_2$ | 2 | H₅ | (CH₂)₂C₆H₅ |
| 40. | 2 | (CH₂)₂ | (CH₂)₂ | CH₂ | $\underset{OH}{\overset{O}{\overset{\|}{C}}}N-CH_3$ | 3 | CH₃ | -cyclohexyl |
| 41. | 3 | CH=CH | (CH₂)₃ | — | CO₂H | 4 | C₂H₅ | C₆H₅ |

-continued

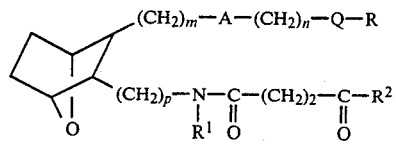

| Ex. No. | m | A | $(CH_2)_n$ | Q | R | p | $R^1$ | $R^2$ |
|---|---|---|---|---|---|---|---|---|
| 42. | 4 | $(CH_2)_2$ | $(CH_2)_4$ | CH=CH | $CO_2H$ | 1 | $C_3H_7$ | $C_7H_{15}$ |
| 43. | 0 | CH=CH | $-CH_2C(F)(F)-$ | $CH_2$ | [tetrazolyl] | 2 | $C_4H_9$ | H |
| 44. | 1 | $(CH_2)_2$ | $-CH_2-C(CH_3)(CH_3)-$ | $-C(F)(F)-$ | $CN(C_2H_5)_2$ (C=O) | 3 | $C_5H_{11}$ | $C_4H_9$ |
| 45. | 2 | CH=CH | $(CH_2)_5$ | $-CH(F)-$ | $CNHC_6H_5$ (C=O) | 4 | H | $-(CH_2)_2CH=CHCH_3$ |
| 46. | 3 | $(CH_2)_2$ | $-CH(CH_3)-CH(F)-$ | $-C(F)(F)-$ | COOH | 1 | H | $C_6H_5$ |
| 47. | 4 | $(CH_2)_2$ | $(CH_2)_2$ | CH=CH | [tetrazolyl] | 2 | H | $-CH_2C_6H_5$ |
| 48. | 0 | CH=CH | $(CH_2)_3$ | $-CH_2-$ | $CO_2CH_3$ | 3 | $CH_3$ | $C_4H_9$ |
| 49. | 2 | $(CH_2)_2$ | $(CH_2)_4$ | $CH_2$ | $CO_2CH_3$ | 4 | $CH_3$ | $C_6H_5$ |
| 50. | 3 | CH=CH | $(CH_2)_5$ | — | $CO_2H$ | 1 | $CH_3$ | $CH_2C_6H_5$ |

What is claimed is:

1. A compound having the structure

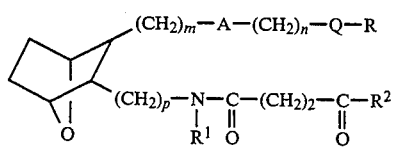

including all stereoisomers thereof, wherein m is 0 to 4; A is —CH=CH— or —CH$_2$—CH$_2$—; n is 1 to 5; Q is —CH=CH—, —CH$_2$—,

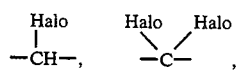

or a single bond; R is $CO_2H$, $CO_2$alkyl, $CO_2$ alkali metal, $CO_2$ polyhydroxyamine salt,

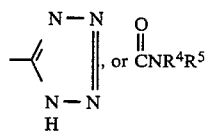

wherein $R^4$ and $R^5$ are the same or different and are H, lower alkyl, hydroxy, lower alkoxy or aryl at least one of $R^4$ and $R^5$ being other than hydroxy and lower alkoxy; p is 1 to 4; $R^1$ is H or lower alkyl; and $R^2$ is H, lower alkyl, lower alkenyl containing 2 to 12 carbons, aryl, arylalkyl, cycloalkyl or cycloalkylalkyl; wherein lower alkyl or alkyl alone or as part of another group contains 1 to 12 carbons and is unsubstituted or substituted with a halo-substituent, such as F, Br, Cl or I or CF$_3$, an alkoxy substituent, an aryl substituent, an alkylaryl substituent, a haloaryl substituent, a cycloalkyl substituent, an alkylcycloalkyl substituent, hydroxy, an amino substituent, an amido substituent, an alkylamino substituent, an arylamino substituent, an alkanoylamino substituent, an arylcarbonylamino substituent, a thioamido substituent, a nitro substituent, a cyano substituent, a thiol substituent, an arylthio substituent or an alkylthio substituent; cycloalkyl alone or as part of another group includes saturated cyclic hydrocarbon groups containing 3 to 12 carbons, which is unsubstituted or substituted with 1 or 2 halogens, 1 or 2 lower alkyl groups 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups; aryl or Ar alone or as part of another group is phenyl or naphthyl, which is unsubstituted or substituted with 1 or 2 lower alkyl groups, halogens selected from the group consisting of Cl, Br, or F, 1 or 2 lower alkoxy groups, 1 or 2 hydroxy groups, 1 or 2 amino groups, 1 or 2 alkylamino groups, 1 or 2 arylamino groups, 1 or 2 alkanoylamino groups, 1 or 2 arylcarbonylamino groups, 1 or 2 amido groups, 1 or 2 nitro groups, 1 or 2 cyano groups, 1 or 2 thioamido groups, 1 or 2 thiol groups, 1 or 2 arylthio groups, and/or 1 or 2 alkylthio groups;

$(CH_2)_m$, $(CH_2)_n$ or $(CH_2)_p$ may independently contain 1 or 2 lower alkyl and/or 1 or 2 halo substituents.

2. The compound as defined in claim 1 wherein $R^2$ is alkyl.

3. The compound as defined in claim 1 wherein A is CH=CH.

4. The compound as defined in claim 1 wherein m is 1 and n is 1 to 4.

5. The compound as defined in claim 1 wherein p is 1.

6. The compound as defined in claim 1 wherein Q is a single bond or $CH_2$.

7. The compound as defined in claim 1 wherein R is $CO_2$ alkyl or $CO_2H$.

8. The compound as defined in claim 1 wherein $R^1$ is H.

9. The compound as defined in claim 1 wherein m is 1, n is 2 to 4, Q is a single bond, R is $CO_2$alkyl or $CO_2H$, p is 1, $R^1$ is H, and $R^2$ is alkyl.

10. The compound as defined in claim 1 having the name [1S-[1β,2α(5Z),3α,4β]]-7-[3-[[(1,4-dioxononyl)amino]methyl]-7-oxabicyclo[2.2.1]hept-2-yl]-5-heptenoic acid or esters thereof, including all stereoisomers thereof.

11. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation or inhibiting bronchoconstriction associated with asthma, which comprises administering to a mammalian host an effective amount of a compound as defined in claim 1 or a pharmaceutically acceptable salt thereof.

15. A method of treating peripheral vascular diseases, which comprises topically or systemically administering to a mammalian host an effective amount of a compound as defined in claim 1 or a pharmaceutically acceptable salt thereof.

* * * * *